(12) United States Patent
Fedurco

(10) Patent No.: US 9,120,725 B2
(45) Date of Patent: Sep. 1, 2015

(54) AROMATIC PERFLUOROALKANE MONOMER

(75) Inventor: Milan Fedurco, Clermont-Ferrand (FR)

(73) Assignees: COMPAGNIE GENERALE DES ESTABLISSEMENTS MICHELIN, Clermont-Ferrand (FR); MICHELIN RECHERCHE ET TECHNIQUE S.A., Granges-Paccot (CH)

( * ) Notice: Subject to any disclaimer, the term of this patent is extended or adjusted under 35 U.S.C. 154(b) by 30 days.

(21) Appl. No.: 13/812,894

(22) PCT Filed: Jul. 6, 2011

(86) PCT No.: PCT/EP2011/061429
§ 371 (c)(1),
(2), (4) Date: May 15, 2013

(87) PCT Pub. No.: WO2012/016780
PCT Pub. Date: Feb. 9, 2012

(65) Prior Publication Data
US 2013/0231405 A1  Sep. 5, 2013

(30) Foreign Application Priority Data
Aug. 4, 2010  (FR) ..................... 10 56440

(51) Int. Cl.
*C07C 309/44* (2006.01)
*C07C 49/825* (2006.01)
(Continued)

(52) U.S. Cl.
CPC .............. *C07C 309/44* (2013.01); *B01D 71/66* (2013.01); *C07C 49/80* (2013.01); *C07C 49/813* (2013.01);
(Continued)

(58) Field of Classification Search
USPC ............................................ 521/27; 568/332
See application file for complete search history.

(56) References Cited

U.S. PATENT DOCUMENTS 6,495,209 B1 12/2002 Cisar ............................ 427/384
7,037,614 B1 * 5/2006 Cooray et al. ................ 429/494
(Continued)

FOREIGN PATENT DOCUMENTS

JP   2001-277720 A   10/2001
WO  WO 2005/006472 A1   1/2005
(Continued)

OTHER PUBLICATIONS

Johnson et al., Journal of the Chemical Society, pp. 4710-4713 (1952).*
(Continued)

*Primary Examiner* — Peter D Mulcahy
*Assistant Examiner* — Henry Hu
(74) *Attorney, Agent, or Firm* — Fitzpatrick, Cella, Harper & Scinto

(57) ABSTRACT

An aromatic perfluoroalkane monomer is provided that can be used for the manufacture of a polymer membrane for a PEM-type fuel cell. The perfluoroalkane monomer has a structure corresponding to a formula (I):

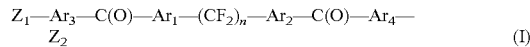

Figure 1A:
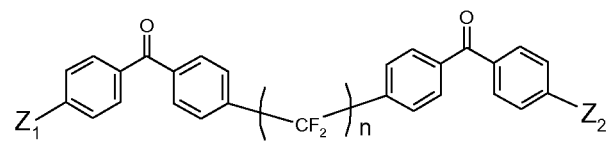

in which:
n is in a range from 1 to 20;
$Ar_1, Ar_2, Ar_3, Ar_4$ which are identical or different, represent a substituted or unsubstituted phenylene group; and
$Z_1$ and $Z_2$, which are identical or different, represent an electrophilic or nucleophilic polymerizable functional group.

14 Claims, 7 Drawing Sheets

(I-1)

(51) Int. Cl.
| | |
|---|---|
| C07C 49/813 | (2006.01) |
| C07C 49/83 | (2006.01) |
| H01M 8/10 | (2006.01) |
| C08G 65/40 | (2006.01) |
| C08L 71/00 | (2006.01) |
| B01D 71/66 | (2006.01) |
| C07C 49/80 | (2006.01) |
| C08G 75/02 | (2006.01) |

(52) U.S. Cl.
CPC .............. *C07C 49/825* (2013.01); *C07C 49/83* (2013.01); *C08G 65/4025* (2013.01); *C08G 75/02* (2013.01); *C08L 71/00* (2013.01); *H01M 8/1025* (2013.01); *H01M 8/1039* (2013.01); *H01M 8/1088* (2013.01); *C08G 2650/40* (2013.01); *Y02E 60/521* (2013.01)

(56) References Cited

U.S. PATENT DOCUMENTS

| | | | |
|---|---|---|---|
| 7,901,821 B2 | 3/2011 | Buchi et al. | 429/429 |
| 2004/0236062 A1* | 11/2004 | Hofmann | 528/125 |
| 2005/0221135 A1* | 10/2005 | Cooray et al. | 429/20 |
| 2008/0160363 A1 | 7/2008 | Tsukada | 429/19 |
| 2010/0040930 A1 | 2/2010 | Delfino et al. | 429/34 |
| 2010/0173227 A1 | 7/2010 | Olsommer | 429/514 |
| 2011/0311899 A1* | 12/2011 | Onodera et al. | 429/482 |

FOREIGN PATENT DOCUMENTS

| | | |
|---|---|---|
| WO | WO 2006/012953 A2 | 2/2006 |
| WO | WO 2006/012954 A1 | 2/2006 |
| WO | WO 2006/100029 A1 | 9/2006 |
| WO | WO 2008/125174 A1 | 10/2008 |
| WO | 2012/016779 A1 | 2/2012 |
| WO | WO-2012/016780 A1 * | 2/2012 |

OTHER PUBLICATIONS

R. Souzy et al., "Functional fluoropolymers for fuel cell membranes," Progress in Polymer Science, vol. 30 (2005), pp. 644-687.

R.D. Spencer et al., "Determination of Four Closely Related Triaryl-s-Triazines by Infrared Spectrometry," Analytical Chemistry, vol. 35, No. 11 (Oct. 1963), pp. 1633-1636.

A.E. Feiring et al., "Fluorinated Poly(ether Sulfone)s," Journal of Polymer Science: Part A: Polymer Chemistry, vol. 28 (1990), pp. 2809-2819.

X. Zhu et al., "Challenging reinforced composite polymer electrolyte membranes based on disulfonated poly(arylene ether sulfone)-impregnated expanded PTFE for fuel cell applications," Journal of Material Chemistry, vol. 17 (2007), pp. 386-397.

D.M. Tigelaar et al., "Synthesis and Properties of Novel Proton-Conducting Aromatic Poly(ether sulfone)s That Contain Triazine Groups," Macromolecules, vol. 42, pp. 1888-1896 (2009).

* cited by examiner (I-1)

(I-2)

(I-3)

(II-1)

(II-2)

(II-3)

Fig. 4
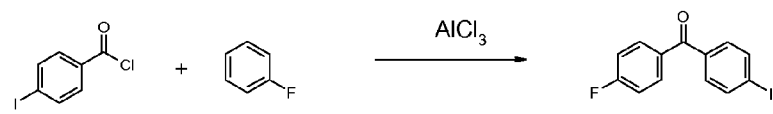
Fig. 4A
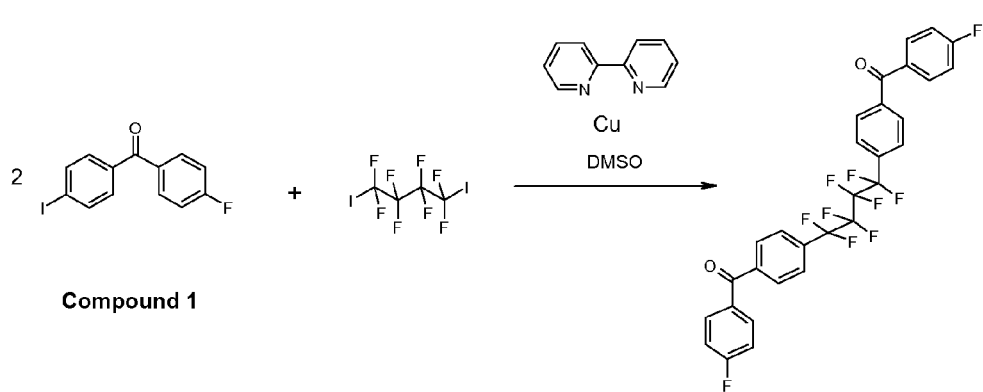
Fig. 4B
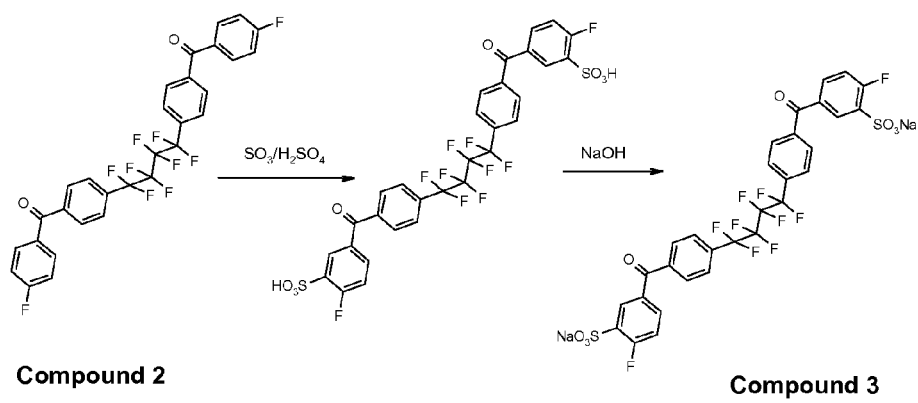
Fig. 4C

Monomer A1

Fig. 6
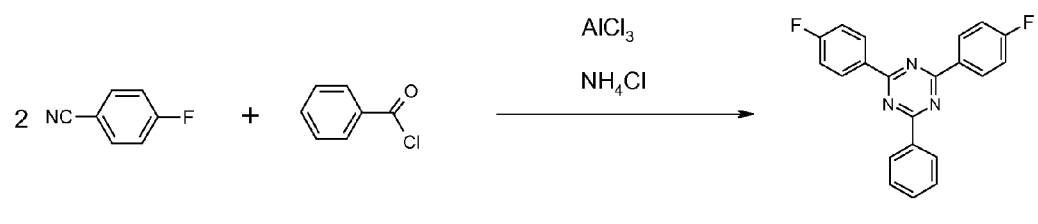
*Fig. 6A*
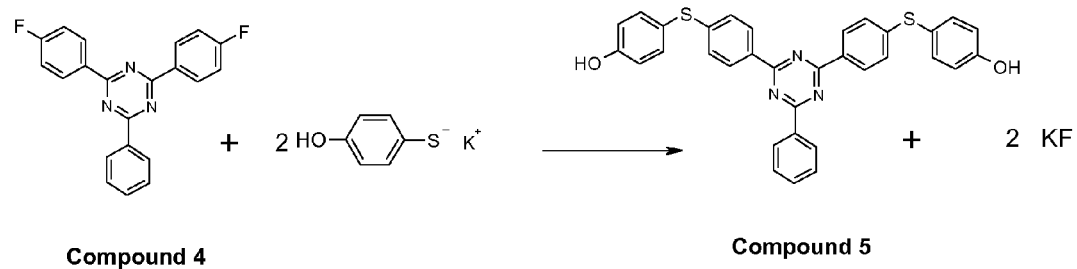
*Fig. 6B*

AROMATIC PERFLUOROALKANE MONOMER

I. FIELD OF THE INVENTION

The present invention relates to the monomers which can be used for the synthesis of polymers intended in particular, in the sulphonated form, to constitute a solid electrolyte or membrane in a fuel cell.

It relates more particularly to the above monomers of the aromatic type comprising a central structural unit of the perfluoroalkylene type.

II. STATE OF THE ART

The recent interest in fuel cells arises from their ability to convert chemical energy into electricity with a relatively high yield and a low emission of environmental pollutants. The use of such electrochemical devices extends today from the motor vehicle industry to portable computers, to mobile phones, to the stationary generation of electrical energy and to other applications comprising exploration of the sea and space.

It should be remembered first of all that a fuel cell is an electrochemical energy generator in which a chemical reaction between hydrogen and oxygen is maintained under control, which reaction will produce water (reverse reaction to electrolysis). It produces electrical energy and heat. The electrolyte therein is typically composed of a PEM (Polymer Electrolyte Membrane) which conducts protons and which is capable of separating the reactive entities, consisting of two very distinct nanophases: on the one hand, a hydrophobic part which provides mechanical integrity, watertightness and gastightness (the gases being $H_2$ and $O_2$) and, on the other hand, a sulphonated part consisting of narrow hydrophilic channels allowing the protons to pass and thus providing the ionic conductivity of the cell. This polymer membrane is positioned between the anode and the cathode of the cell, such an assembly being commonly referred to as "MEA" (Membrane Electrode Assembly).

Such fuel cells, MEA assemblies and their general operating principles are well known. They have been described in a very large number of documents; mention may be made, as examples, of the general article entitled *"Functional fluoropolymers for fuel cell membranes"* by Renaud Souzy & Bruno Ameduri, Prog. Polymer Sci., 30 (2005), 644-687, and Patent Applications WO 2005/006472, WO 2006/012953, WO 2006/012954, WO 2006/100029 and WO 2008/125174.

A polymeric material which is a good candidate for a PEM fuel cell must meet very high requirements as regards its mechanical, physical and chemical properties. Ideally, the MEA assembly is expected to be able to operate for thousands of hours at relatively high temperatures (60 to 100° C. in the case of PEM cells, up to 160° C. in the case of methanol cells referred to as DMFCs) while being exposed to particularly high humidity and acidic pH values close to zero. The majority of known polymers undergo decomposition under such conditions, whether of aliphatic type or of aromatic type.

Aliphatic copolymers derived from perfluorosulphonic acid, sold, for example, under the Nafion® or Flemion® name, have been intensively employed as conducting membranes in fuel cells of the hydrogen/air, hydrogen/oxygen or methanol/air type.

Despite a very good ion conductivity and a high chemical stability, the use of polymers of the Nafion® type is first of all not suited to employment in fuel cells of the methanol type, due to reduced performance for the highest operating temperatures, due to a significant increase in permeability of the membrane with regard to the methanol.

Another known disadvantage of the polymers of the Nafion® type, in operation in the cell, is their relatively limited chemical stability. This is because perfluoropolymers are known to absorb large amounts of water responsible for repeated dimensional changes and swellings of the membrane: repeated cycles of drying and humidification, during successive shutdowns and startups of the fuel cell, result in an increased permeability to gases ($H_2$ and $O_2$); this increased permeability is responsible for the formation of hydrogen peroxide and free radicals (OH), so many mechanisms which can result in rapid degradation in a membrane and in the premature end of life of the fuel cell. In order to limit these dimensional changes and to thus improve the endurance of the membranes, it has been proposed in particular to add, as reinforcing polymer, a second fluoropolymer, in particular a PTFE (polytetrafluoroethylene) of the expanded microporous (or "ePTFE") type, and to thus form tougher composite membranes (see, for example, U.S. Pat. No. 6,495,209).

Finally, another major disadvantage of the polymers of the Nafion® type is the cost of their synthesis, without mentioning a base chemistry which no longer corresponds today to the most recent requirements in terms of the environment and of health and safety regulations.

Consequently, much research has been carried out in the past in an attempt to reduce the cost of the PEM membranes.

It has in particular been proposed to replace the above aliphatic polymers with aromatic polymers, which are lower in cost and which furthermore have the advantage of exhibiting a reduced permeability to the gases ($H_2$ and $O_2$).

Examples of such polymers are, for example, poly(arylene-ether-sulphone)s, sold in particular under the "Udel" or "Radel" names, or poly(ether-ether-ketone)s, sold, for example, under the "PEEK" name. The above aromatic polymers, once sulphonated, still do not make it possible today to achieve the compromise in performance and in cost offered with the fluorinated aliphatic polymers of the Nafion® type. In addition, these aromatic polymers generally mix poorly with an ePTFE-type polymer and the membranes which result therefrom thus cannot be easily reinforced with an ePTFE polymer, such a reinforcing requiring a preliminary surface treatment of the ePTFE polymer by plasma or by the chemical route in very aggressive chemical media (see, for example, the paper entitled *"Challenging reinforced composite polymer electrolyte membranes based on disulfonated poly(arylene-ether-sulfone)-impregnated expanded PTFE for fuel cell applications"*, Xiaobing Zhu et al., J. Mat. Chem., 2007, 386-397).

Other examples of polymers of the aromatic type have been described more recently in the patent documents US2005/0221135 and U.S. Pat. No. 7,037,614. They are sulphonated triazine polymers, the monomers of which are connected via ether (—O—) bridges. The syntheses described in these documents are complex, expensive and difficult to reproduce. In addition, it has been found that their chemical and dimensional stability is insufficient even after a final crosslinking treatment of the membranes, which treatment furthermore requires another complex and expensive chemistry.

III. BRIEF DESCRIPTION OF THE INVENTION

During their research studies, the Applicant Companies have found a novel aromatic monomer, more precisely a specific aromatic perfluoroalkane monomer, which can be used for the synthesis of a polymer membrane making it possible to overcome, at least in part, the abovementioned disadvantages.

This aromatic perfluoroalkane monomer of the invention, corresponds to the formula (I):

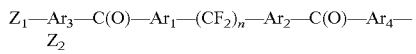
Z₂ in which:
n is in a range from 1 to 20;
the symbols $Ar_1$, $Ar_2$, $Ar_3$ and $Ar_4$, which are identical or different, represent a substituted or unsubstituted phenylene group;
the symbols $Z_1$ and $Z_2$, which are identical or different, represent an electrophilic or nucleophilic polymerizable functional group.

Starting from this monomer in accordance with the invention, it has proven possible to synthesize a polymer which, in comparison with the polymers of the prior art described above, has a markedly improved chemical stability and a markedly improved resistance to oxidation. It makes it possible to manufacture PEM membranes which, unexpectedly, in comparison with commercial membranes of the Nafion® type already developed a long time ago, exhibit a chemical stability and a dimensional stability which are at least equivalent, and an ion conductivity approaching that of these commercial membranes. Finally, the polymer resulting from the monomer of the invention can, which is not the least of its advantages, be rendered compatible with a microporous ePTFE polymer for optimal reinforcing of the membrane, without requiring the surface treatments which were mentioned above.

The invention also relates to a process for the synthesis of a polymer by polycondensation of at least one aromatic perfluoroalkane monomer in accordance with the invention.

The invention also relates to the use of an aromatic perfluoroalkane monomer in accordance with the invention for the manufacture of a polymer membrane which can be used in a fuel cell of the PEM type.

Figure 7:
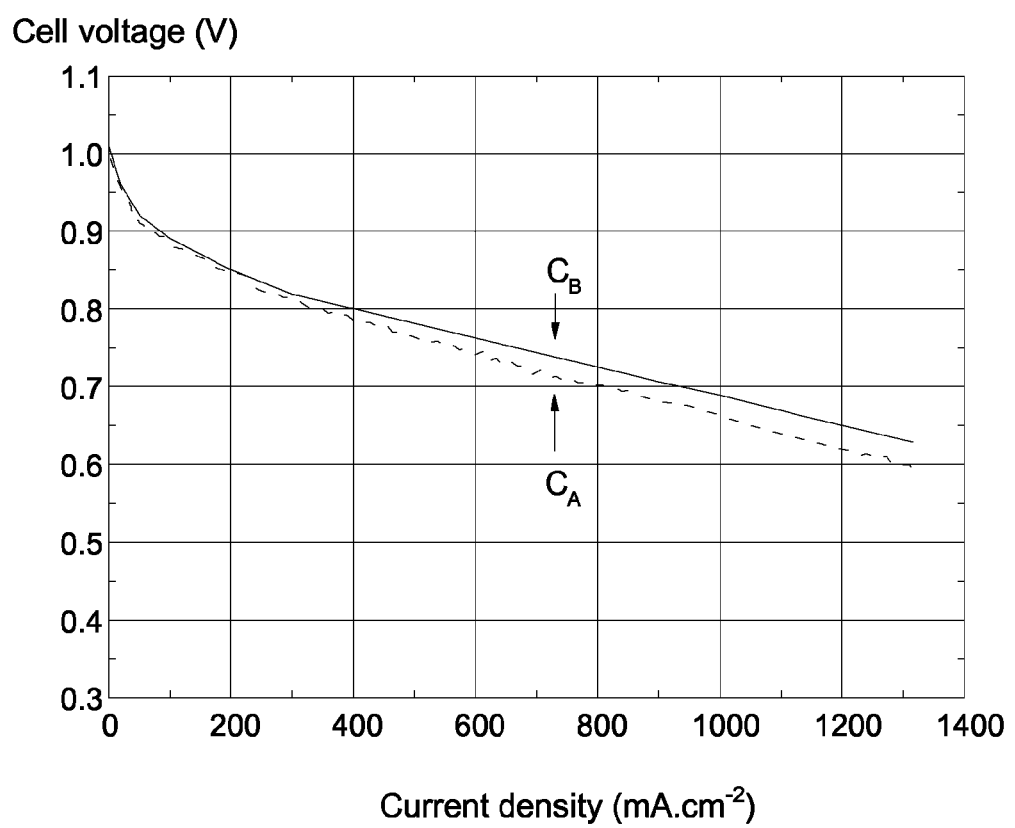

The invention and its advantages will be easily understood in the light of the detailed description and implementational examples which follow, and also of the figures relating to these examples, which represent or schematize:
examples of monomers in accordance with the invention of formula (I), of respective specific formulae (I-1), (I-2) and (I-3) (FIGS. 1A, 1B and 1C);
examples of monomers in accordance with the invention of formula (I), of respective specific formulae (II-1), (II-2) and (II-3) (FIGS. 2A, 2B and 2C);
an example of a polymer (Polymer 1) and also a possible scheme for the synthesis of this polymer by polycondensation of a monomer A1 in accordance with the invention with a second monomer B1 not in accordance with the invention (FIG. 3);
a possible scheme for the synthesis, in three successive stages, of the monomer A1 (or Compound 3) in accordance with the invention (FIG. 4);
the ¹H NMR spectrum (500 MHz) of the monomer A1 (or Compound 3) dissolved in $d_6$-DMSO (FIG. 5);
a possible scheme for the synthesis, in two successive stages, of the monomer B1 (or Compound 4) not in accordance with the invention (FIG. 6);
comparative polarization curves of a PEM fuel cell using the membrane resulting from the Polymer 1 (curve $C_A$) and a commercial membrane (curve $C_B$) (FIG. 7).

IV. DETAILED DESCRIPTION OF THE INVENTION

The aromatic perfluoroalkane monomer of the invention thus has the essential characteristic of corresponding to the formula (I):

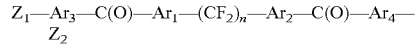
Z₂ in which:
n is in a range from 1 to 20;
the symbols $Ar_1$, $Ar_2$, $Ar_3$ and $Ar_4$, which are identical or different, represent a substituted or unsubstituted phenylene group;
the symbols $Z_1$ and $Z_2$, which are identical or different, represent an electrophilic or nucleophilic polymerizable functional group.

In other words, the perfluoroalkane monomer of formula (I) above is a benzophenone perfluoroalkane monomer having the expanded formula:

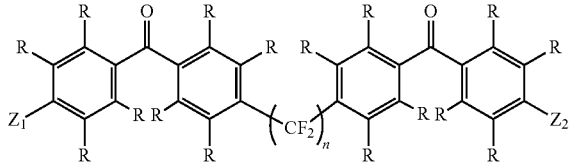

in which R represents hydrogen or a replacement for the hydrogen.

In the formula (I) above and all the preferred alternative forms of the invention described in the present patent application, n preferably varies from 2 to 20, more preferably from 2 to 8; more particularly still, the perfluoroalkane monomer of the invention is a perfluorobutane monomer, that is to say that n is equal to 4.

As indicated above, the phenylene groups $Ar_1$, $Ar_2$, $Ar_3$ and $Ar_4$ of the two benzophenone structures can be substituted or unsubstituted. When they are substituted, the invention applies in particular to the cases where just one phenylene group per monomer of formula (I) is substituted as well as to the cases where several phenylene groups per monomer are substituted, it being possible for just one substituent or several identical or different substituents to be present on the or the same phenylene group(s).

Mention may in particular be made, as examples of possible substituents of the aromatic nuclei (that is to say, more precisely possible replacements for the hydrogen atoms of these phenylene groups), of the following substituents:
—F; —Cl; —Br; —CN; —CF₃; —NO₂; —N(CH₃)₂;
—COOH; —COOM; —PO₃H; —PO₃M; —SO₃H;
—SO₃M (the symbol M representing an alkali metal cation, preferably Na⁺ or K⁺);
hydroxyl, alkyl, cycloalkyl, perfluoroalkyl, sulphoalkyl, sulphoaryl, aryl, alkylcarbonyl, arylcarbonyl, alkoxyl or aryloxyl radicals.

These possible substituents are preferably selected from the group consisting of the substituents —F, —CN, —CF₃, —PO₃H, —PO₃M, —SO₃H and —SO₃M and the mixtures of these substituents.

Figure 1B:
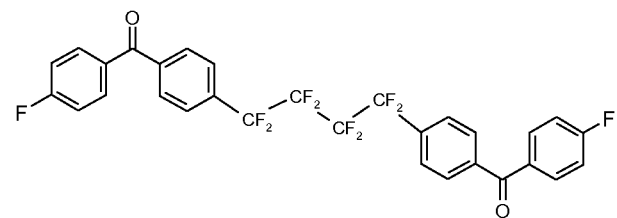
Figure 1C:
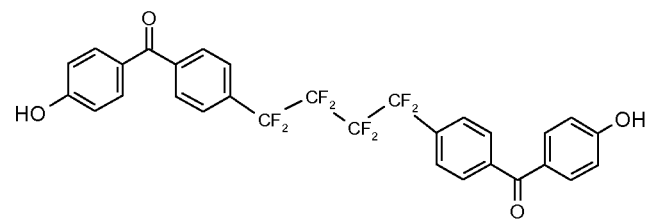

In the specific case where R is hydrogen, that is to say when none of the phenylene groups is substituted, then the aromatic perfluoroalkane monomer of the invention corresponds to the formula (I-1) as represented in the appended FIG. 1A.

$Z_1$ and $Z_2$, which are identical or different, represent an electrophilic or nucleophilic functional group.

Such polymerizable functional groups are well known to a person skilled in the art: to remind, an electrophilic functional group or group (atom or group of atoms) (Lewis acid or electron acceptor) has a missing pair of electrons and is thus capable of creating a covalent bond with a Lewis base; conversely, a nucleophilic functional group or group (atom or group of atoms) (Lewis base or electron donor) has a free pair of electrons and is thus capable of creating a covalent bond with a Lewis acid.

More preferably, $Z_1$ and $Z_2$, which are identical or different, are selected from the group consisting of halogens (such as F, Cl, Br or I), hydroxyl (OH), alkoxyls (OR), thiol (SH), carboxyl (COOH), carboxylates (COOR), thiol (SH), amino ($NH_2$), sulphonamido ($SO_2$—$NH_2$), acyl chloride (CO—Cl), sulphonyl chloride ($SO_2$—Cl), sulphonyl fluoride ($SO_2$—F), isocyanate (NCO) and the mixtures of such functional groups.

More preferably still, $Z_1$ and $Z_2$, which are identical or different, are selected from the group consisting of halogens (such as F, Cl, Br or I), hydroxyl (OH), thiol (SH), and the mixtures of such functional groups.

According to an even more preferred embodiment, the $Z_1$ and $Z_2$ groups correspond to the hydroxyl group or to a halogen, in particular fluorine or chlorine.

Thus, according to a first particularly preferred embodiment, the $Z_1$ and $Z_2$ groups correspond to the halogen fluorine in the formula (I). In the more preferred specific case where the central perfluoroalkylene block is a perfluorobutylene, the aromatic perfluoroalkane monomer of the invention is thus 1,4-bis(4-fluorobenzophenone) perfluorobutane, corresponding to the formula (I-2) represented in the appended FIG. 1B, in which the phenylene groups can be substituted or unsubstituted.

According to a second particularly preferred embodiment, the $Z_1$ and $Z_2$ groups correspond to hydroxyl in the formula (I). Thus, in the more preferred specific case where the central perfluoroalkylene block is a perfluorobutylene, the aromatic perfluoroalkane monomer of the invention of formula (I) is thus 1,4-bis(4-hydroxybenzophenone)perfluorobutane corresponding to the formula (I-3) represented in the appended FIG. 1C, in which the phenylene groups can be substituted or unsubstituted.

The aromatic perfluoroalkane monomer in accordance with the invention described above can advantageously be used for the synthesis of polymers which can form, in the sulphonated form, an electrolyte (or membrane, which is equivalent) in a fuel cell. The term "polymer" should be understood as meaning any homopolymer or copolymer, in particular block copolymer, comprising at least structural units resulting from the monomer of the invention.

The term "sulphonated monomer" or "sulphonated polymer" is understood to mean, by definition and in a well known way, a monomer or polymer bearing one or more sulphonic (—$SO_3H$) or sulphonate (—$SO_3M$) groups or mixtures of such groups, M representing a cation of an alkali metal preferably selected from lithium (Li), caesium (Cs), sodium (Na) and potassium (K), more preferably from sodium (Na) and potassium (K). It will be restated briefly here that it is the sulphonic groups which, in a PEM cell, provide the proton conductivity of the polymer used as membrane.

The invention relates in particular to a perfluoroalkane monomer as described above in which at least one sulphonic or sulphonate group is borne by at least one of its phenylene groups or, if appropriate, by at least one of the substituents of its phenylene groups. The term "bearing phenylene group" should thus be understood as meaning, in the present patent application, that the phenylene group itself or one of the optional replacements for its hydrogen atoms bears a sulphonic or sulphonate group.

Figure 2A:
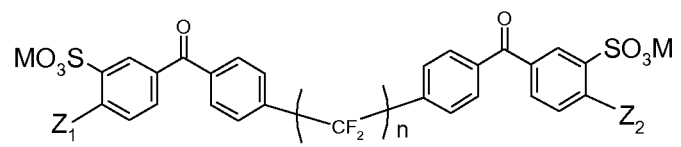
Figure 2B:
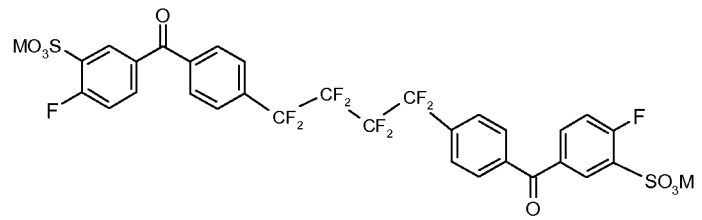
Figure 2C:
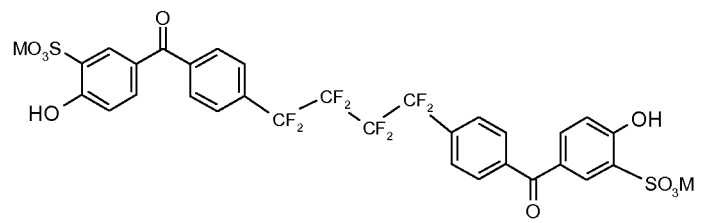

Examples of monomers according to the invention in the sulphonated form in which at least one phenylene group per benzophenone group bears a sulphonate group —$SO_3M$ (M representing an alkali metal cation preferably selected from Li, Cs, Na and K, more preferably from Na and K) are illustrated in FIGS. 2A, 2B and 2C:

a sulphonated aromatic perfluoroalkane monomer of formula (II-1) (FIG. 2A);

an alkali metal salt of 1,4-bis(4-fluorobenzophenone) perfluorobutane disulphonate, in which the $Z_1$ and $Z_2$ groups correspond to the halogen fluorine and the perfluoroalkane central block is a perfluorobutylene (FIG. 2B);

an alkali metal salt of 1,4-bis(4-hydroxybenzophenone) perfluorobutane disulphonate, in which the $Z_1$ and $Z_2$ groups correspond to hydroxyl and the perfluoroalkylene central block is a perfluorobutylene (FIG. 2C).

Figure 3:
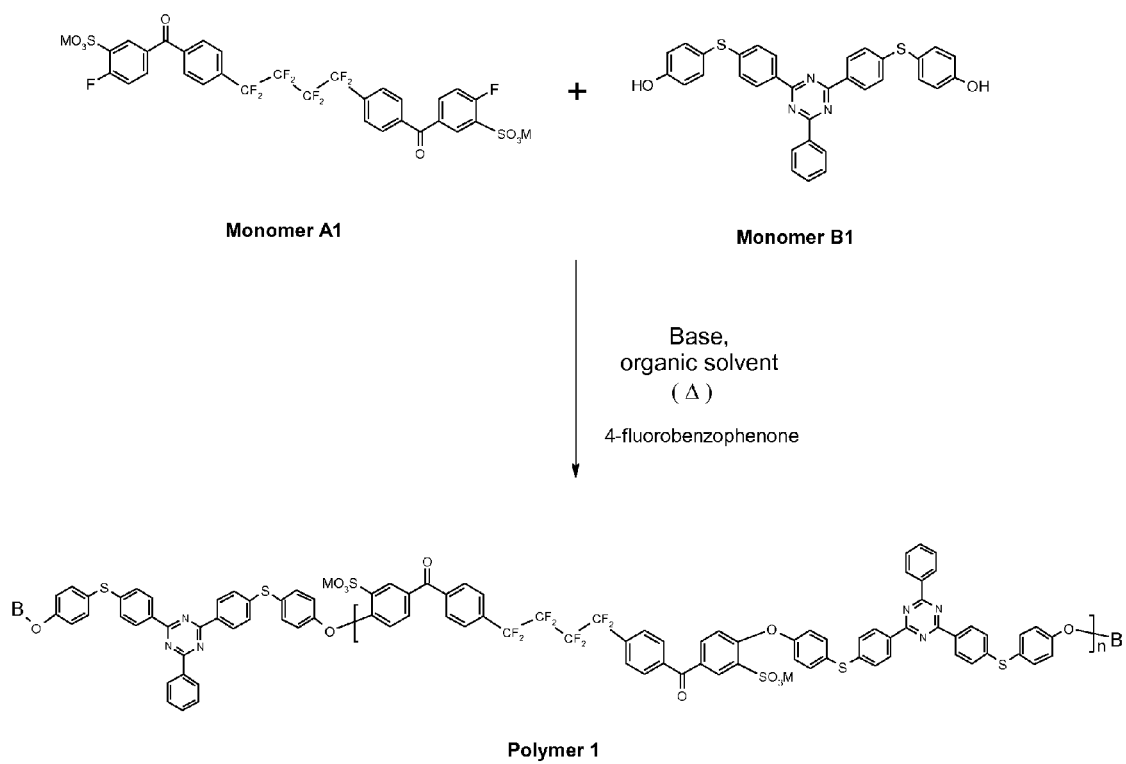

An example of a polymer which can be synthesized from an aromatic perfluoroalkane monomer in accordance with the invention and also a possible scheme for the synthesis of this polymer from such a monomer are represented in the appended FIG. 3.

The triazine polymer (hereinafter referred to as "Polymer 1") as represented in FIG. 3 (in the sulphonated form) is composed of two types of structural units connected to one another via ether (—O—) bridges. This Polymer 1 can be prepared by polycondensation of a monomer in accordance with the invention, denoted A1 (in this instance, in the disulphonate form), with a triazine monomer not in accordance with the invention, denoted B1 in FIG. 3, in the presence of a base and of an organic solvent, according to a procedure which will be described in detail later. The monomer A1 in accordance with the invention corresponds to the aromatic perfluorobutane monomer of formula (II-2) described above (FIG. 2B).

It should be noted that this Polymer 1 of FIG. 3, in the sulphonated form, is composed of structural units based on aromatic perfluoroalkane (benzophenone) and of triazine units connected to one another via ether (—O—) bridges. In this instance, the Polymer 1 comprises chain ends blocked by benzophenone blocking groups (B in FIG. 3), which are hydrophobic and sterically hindering and which are intended to reduce the solubility of the polymer in water.

V. EXAMPLES OF THE IMPLEMENTATION OF THE INVENTION

The tests which follow first of all describe in detail the synthesis of the monomers A1 (in accordance with the invention) and B1 (not in accordance with the invention) and then that of the Polymer 1. Subsequently, the Polymer 1 is characterized and tested as a proton-conducting membrane in a fuel cell of the PEM type.

In the present description, unless expressly indicated otherwise, all the percentages (%) shown are % by weight.

V-1. Synthesis of the Monomer A1

The monomer A1 is disulphonated 1,4-bis(4-fluorobenzophenone)perfluorobutane, the formula of which is as follows:

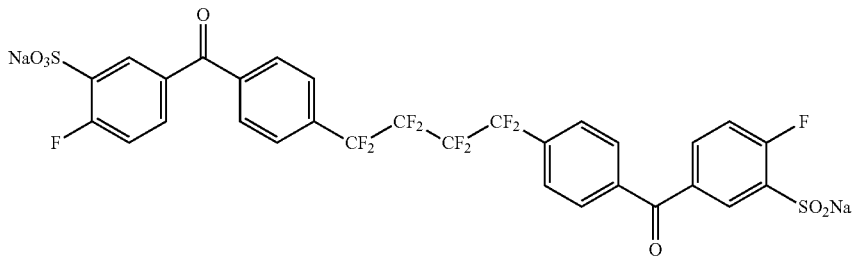

This monomer A1 in accordance with the invention (or Compound 3) was prepared according to the procedure represented diagrammatically in FIG. 4, in three successive stages, as described in detail below.

V-1-A) Stage 1

During a first stage, the Compound 1 or (4-fluorophenyl)(4-iodophenyl)methanone is prepared in accordance with FIG. 4A.

4-Iodobenzoyl chloride (30 g, i.e., 112.6 mmol), aluminium chloride (15.0 g, i.e., 112.7 mmol) and fluorobenzene (21.7 g, i.e., 225.8 mmol) are added to a predried 250 ml round-bottomed flask. The mixture is stirred at ambient temperature under a gentle stream of nitrogen overnight. The following day, a solid has appeared and stirring is no longer possible. An additional 20 ml of fluorobenzene are then added and the reactants are mixed at 40° C. (temperature inside the round-bottomed flask) for 3 h. The apparatus is placed at 40° C. under vacuum (water pump) and the excess fluorobenzene is distilled off (for 30 min).

200 g of ice are directly added to the round-bottomed reaction flask, followed immediately by 60 ml of 37% HCl. The solid product thus obtained is reduced to a powder in a ceramic mortar, then stirred in water until a white powder is obtained, finally separated from the HCl solution by filtration (filter paper) and washed until a neutral pH is obtained. The solid is dried at ambient temperature (23° C.) using the water pump, then mixed with 200 ml of ethanol and finally heated at 60° C. (temperature inside the round-bottomed flask) until everything is dissolved. The compound is finally precipitated by cooling the ethanol at ambient temperature.

The final product (approximately 30 g) is purified by silica (300 g) chromatography using a hexane/ethyl acetate mixture (ratio by weight 16/4) as mobile phase. The product is separated from the mobile phase on a rotary evaporator and dried at 80° C. overnight (under vacuum). The final cream-coloured product (25 g) proves to be pure by NMR analysis and TLC chromatography in the hexane/ethyl acetate (ratio 16/4) mixture, with a melting point (measured by DSC) of approximately 137° C.

The Compound 1, of formula:

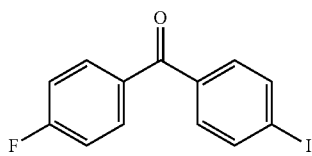 [SMILES: O=C(c1ccc(F)cc1)c1ccc(I)cc1]

is thus obtained.

The NMR analysis gives the following results:
$^1$H NMR, 500 MHz (CD$_2$Cl$_2$): 7.17-7.20 (m, 2H), 7.48-7.50 (m, 2H), 7.80-7.82 (m, 2H), 7.87-7.89 (m, 2H).

V-1-B) Stage 2

Then, during a second stage, the Compound 2 or 1,4-bis(4-fluorobenzo-phenone)perfluorobutane is prepared according to the procedure which follows and which is represented diagrammatically in FIG. 4B.

17.0 g of 4-iodo-4'-fluorobenzophenone (i.e., 52.13 mmol), 2.0 g of 2,2'-bipyridyl (i.e., 12.83 mmol), followed by 11.83 g of 1,4-diiodoperfluorobutane (i.e., 26.06 mmol) and 150 ml of anhydrous DMSO, are introduced into a predried 500 ml four-necked round-bottomed flask. Subsequently, 6.60 g of copper powder are added and the solution is heated at 65° C. (the oil bath is regulated at 74° C.) for 5 h under a nitrogen stream with continual stirring.

The reaction mixture is cooled to ambient temperature and then poured into 500 ml of cold water; the product precipitates and then it is filtered off and dissolved with 1 liter of dichloromethane. The organic phase is subsequently dried with anhydrous Na$_2$SO$_4$. The final product is purified by silica (300 g) chromatography in a dichloromethane/cyclohexane (1/1) mixture.

The Compound 2 in the form of a white powder, of formula:

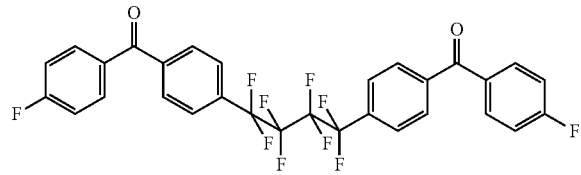 [SMILES: O=C(c1ccc(F)cc1)c1ccc(C(F)(F)C(F)(F)C(F)(F)C(F)(F)c2ccc(C(=O)c3ccc(F)cc3)cc2)cc1]

is thus obtained.

The NMR analysis gives the following results:
$^1$H NMR, 500 MHz (CD$_2$Cl$_2$): 7.19-7.23 (m, 2H), 7.73-7.75 (d, 4H), 7.83-7.87 (m, 8H). $^{19}$F NMR, 471.3 MHz (CDCl$_3$): 105.04 (m, 2F), 111.44-111.50 (d, 4F), 121.49-121.55 (m, 4F).

The melting point of the product (measured by DSC) is equal to approximately 222° C.

V-1-C) Stage 3

Finally, during a third and final stage, the Compound 3 or disulphonated 1,4-bis(4-fluoro-benzophenone)perfluorobutane is prepared according to the procedure which follows and which is represented diagrammatically in FIG. 4C.

The Compound 2 (2.5 g, i.e., 4.18 mmol) is placed in a 50 ml four-necked round-bottomed flask dried beforehand using a hot-air gun and placed under a stream of nitrogen. 6 g of sulphuric acid (distilled twice, Sigma-Aldrich) and 10 g of oleum (65%, Merck) are added directly to the solid. The reaction medium immediately becomes dark. The exiting gaseous products are purged in an empty glass trap, followed by a trap filled with 30% NaOH. The reaction medium is heated at approximately 130° C. (approximately 138° C. in the oil bath) for 4 h under a moderate stream of nitrogen moving above the solution.

Once the sulphonation is complete, the reaction mixture is allowed to cool to ambient temperature and then it is poured into 63 g of ice and left stirring. Once all the ice has melted, 6.25 g of NaCl are added. The solution is heated at 100° C. and then cooled to ambient temperature in order for the sulphonated monomer to precipitate. The precipitate is subsequently again dissolved in 15 ml of water and again heated at 100° C. in order to convert it back into the liquid form. Once all the product has dissolved, the pH is adjusted to 7.0 by adding 10% NaOH (aq.) dropwise. The solution is allowed to cool to ambient temperature. The cream white solid thus obtained is separated from the aqueous phase by filtration. The product is dried at 150° C. overnight (under vacuum).

The Compound 3 (monomer A1), of formula:

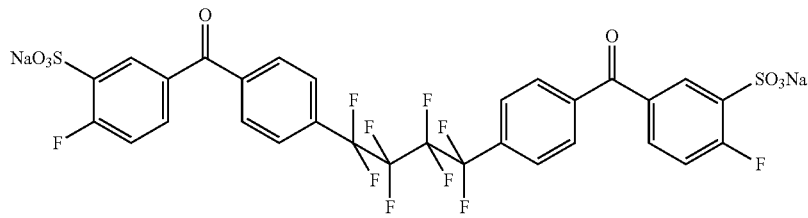

is thus obtained.

Figure 5:
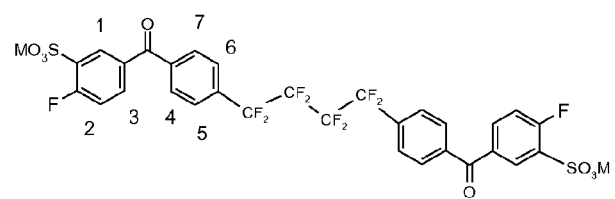
Figure 5:
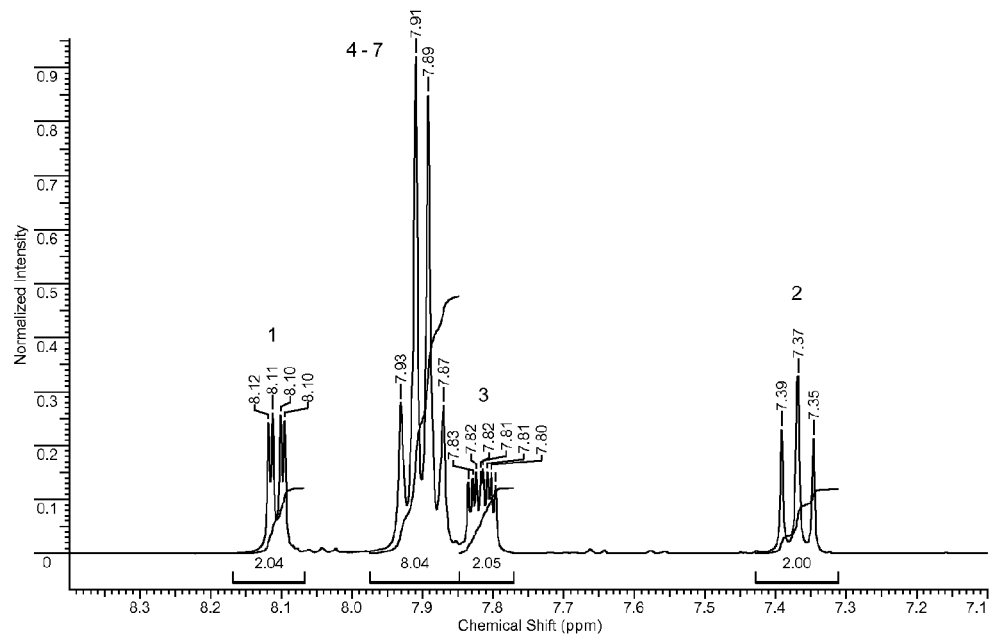

The $^1$H NMR spectrum (500 MHz) of the monomer A1 thus obtained, dissolved in $d_6$-DMSO, is reproduced in FIG. 5.

The NMR analysis gives the following results:
$^1$H NMR, 500 MHz ($d_6$-DMSO): 7.35-7.39 (m, 2H), 7.80-7.83 (m, 2H), 7.87-7.93 (m, 8H), 8.09-8.10 (d, 1H), 8.11-8.12 (d, 1H).

Finally, the molecular weight of the product, as measured by "ESI" (Electrospray Ionization) mass spectrometry (negative mode; water/acetone 1/1 mixture), is equal to 778.9 (calculated theoretical value equal to 779.6).

V-2. Synthesis of the Monomer B1

This monomer B1 not in accordance with the invention (or Compound 5 in FIG. 6) was prepared according to the procedure represented diagrammatically in FIG. 6, in two successive stages, as described in detail below.

V-2-A) Stage 1

During a first stage, the Compound 4 or 2,4-bis(p-fluorophenyl)-6-phenyl-1,3,5-triazine is prepared according to the procedure which follows and which is represented diagrammatically in FIG. 6A.

This procedure, although different, is inspired by the process for the synthesis of chlorinated triphenyltriazines as described in the publication by Spencer R. D. & Beggs B. H, "*Determination of Four Closely Related Triaryl-s-Triazines by Infrared Spectroscopy*", Anal. Chem., 1963, 31(11), 1633-1636.

A 500 ml three-necked round-bottomed flask, equipped with a magnetic bar, a reflux condenser and a thermometer, is dried using a hot-air gun (the apparatus is placed under vacuum). 67.8 g of p-fluorobenzonitrile (0.56 mol) (Fluorochem 99%), 36.0 g of ammonium chloride (0.68 mol), 34.0 g of aluminium chloride (0.26 mol) and 32.0 g of benzoyl chloride (0.22 mol) are placed in the round-bottomed flask under nitrogen. The round-bottomed flask is immersed in an oil bath heated to 158° C. and is left overnight at 150° C. (temperature inside the reaction round-bottomed flask), a gentle stream of nitrogen placed above the reaction mixture.

The reaction product is cooled to ambient temperature (approximately 23° C.) and hydrolysed by adding 300 g of ice and 60 g of 36% HCl. The solid is filtered off, then dispersed in water and washed until a neutral pH is obtained. The white solid is stirred in 500 ml of methanol heated at reflux for 30 min and then the mixture is allowed to cool to ambient temperature. To finish, the product is filtered off and dried at 60° C. under vacuum.

26.6 g (yield 35%) of Compound 4 are thus obtained, exhibiting a melting point (according to DSC) of 254.5° C.

The NMR analysis gives the following results:
$^1$H NMR, 500 MHz ($CD_2Cl_2$): 7.30-7.34 (m, 4H), 7.62-7.65 (m, 2H), 7.68-7.70 (m, 1H), 8.79-8.80 (d, 2H), 8.82-8.85 (m, 4H).

V-2-B) Stage 2

During a second stage, the Compound 5 or 2,4-[4-(4-hydroxyphenylsulphanyl)phenyl]-6-phenyl-1,3,5-triazine is prepared according to the procedure which follows and which is represented diagrammatically in FIG. 6B.

4-Hydroxythiophenol (or 4-HTP) (99%, Acros) is stored under nitrogen and in solid form. The Compound 4 and $K_2CO_3$ are dried separately overnight at 150° C. under vacuum. A magnetic bar is placed in a 2l round-bottomed flask (equipped with a reflux condenser, a thermometer and a nitrogen inlet/outlet). The apparatus is placed under vacuum and dried. A two-way valve is used to replace the vacuum with nitrogen and to continually purge with the inert gas during the addition of the reactants.

The Compound 4 (9.13 g, i.e., 26.44 mmol) and powdered anhydrous $K_2CO_3$ (9.69 g, i.e., 1.2 eq. with respect to the 4-HTP) are added, while still hot (at the end of drying), to the apparatus purged with nitrogen. This is followed by the addition of 750 ml of anhydrous DMSO. The suspension obtained is subsequently purged for at least 15 min with a stream of nitrogen inside the solution.

The required amount of 4-HTP (7.45 g or 58.42 mmol, i.e., 2.2 eq.), in the liquid form, is transferred using a 10 ml plastic syringe, weighed directly inside the syringe and injected into the reaction mixture. Once all the reactants are added, the nitrogen is purged continuously above the solution. The mixture is heated at 100° C. overnight (20 hours) with continuous stirring and is then allowed to cool to ambient temperature.

The product cannot be purified in a single stage: approximately 250 ml of aliquot fraction of the reaction mixture are withdrawn and poured into a separation funnel (3 liters) containing 2.6 liters of ethyl acetate/water (ratio by weight 1/1). The remainder of the product is kept under a continual stream of nitrogen. The mixture placed in the separation funnel is shaken (the colour changes from orange to lemon yellow) and the desired product is extracted into the ethylene acetate phase (the $DMSO/H_2O$ phase comprises only traces of the desired product). The organic phase is washed with 100 ml of an $NaHCO_3$ solution, which stage is followed by washing with 100 ml of $H_2O$; the organic phase is subsequently dried with anhydrous $MgSO_4$. The process is repeated twice with the other two remaining 250 ml aliquots of the reaction mixture.

The ethyl acetate phase is evaporated using a rotary evaporator; a viscous slightly orange liquid, like honey, remains (comprising a small amount of DMSO). The residual DMSO is removed at 100° C. under reduced pressure. A small amount of acetone (10 ml) is added, followed by 40 ml of diethyl ether. The solid immediately becomes cream white and is filtered off on a ceramic filter. The residual thiol is removed from the reaction product by column chromatography using hexane/$CH_2Cl_2$/ethyl acetate/methanol (ratios by weight 4/2/1/1) as mobile phase.

13.1 g (i.e., a yield of approximately 89%) of the Compound 5 are thus obtained.

The NMR analysis gives the following results:
$^1$H NMR (500 MHz) $d_6$-DMSO: 6.93-6.95 (d, 4H), 7.17-7.19 (d, 4H), 7.42-7.44 (d, 4H), 7.58-7.60 (m, 2H), 7.65-7.68 (m, 1H), 8.49-8.50 (d, 4H), 8.61-8.63 (d, 2H), 10.04 (s, 2H).

The molecular weight of the product, as measured by "MALDI" (Matrix-assisted Laser Desorption/Ionization) mass spectrometry (positive mode; dithranol matrix), is equal to 558.1 (calculated theoretical value equal to 557.7).

V-3. Synthesis of the Polymer 1

This example describes in a detailed way the synthesis of the Polymer 1, according to a process already commented on in FIG. 3, from the Monomer A1 (or Compound 3) in accordance with the invention and the Monomer B1 (or Compound 5) not in accordance with the invention as described above, this Polymer 1 being obtained here, on the one hand, in the sulphonated form and, on the other hand, in the form blocked by benzophenone groups.

The Monomer A1 and $Na_2CO_3$ are first of all dried separately at 150° C. overnight (under vacuum) and then they are mixed together at 160° C. for 1 h. The Monomer B1 is itself also dried at 80° C. (under vacuum) overnight.

The polymerization is carried out in a 100 ml three-necked round-bottomed flask. The round-bottomed flask is surmounted by a nitrogen inlet, a thermometer, a stirrer and a Dean & Stark separator surmounted by a reflux condenser. The glass parts of the apparatus (including the reflux condenser and the Dean Stark) are dried under vacuum using a hot-air gun. The round-bottomed flask is charged with the Monomer B1 (0.848 g, i.e., 1.52 mmol), the Monomer A1 (1.22 g, i.e., 1.52 mmol), anhydrous sodium carbonate (0.48 g, i.e., 4.57 mmol; three times the excess), dry N,N-dimethylacetamide (DMA) (20 ml) and toluene (4 ml; azeotropic agent). The round-bottomed reaction flask is heated in an oil bath at 100° C. The temperature of the oil bath is subsequently increased to approximately 148° C. and the residual toluene is distilled off (140° C. inside the round-bottomed reaction flask).

The trap of the Dean Stark is emptied (toluene extracted) and the temperature of the oil bath is increased to approximately 159° C. (approximately 150° C. inside the round-bottomed flask) and is then maintained at this temperature overnight (20 h in total).

The temperature of the reaction is then lowered to 100° C. inside (the round-bottomed flask is raised above the oil bath) and then 4 mg of 4-fluorobenzophenone dissolved in 5 ml of DMA are injected into the reaction using a syringe. The blocking reaction is subsequently continued in an oil bath regulated at approximately 145° C. (internal temperature) for 4 h. The reaction mixture is allowed to cool to ambient temperature and then the polymer is poured into 300 ml of 2-propanol. The fibrous precipitate is recovered by filtration and dried in an oven at 80° C. overnight (under vacuum). The sodium carbonate is removed from the polymer by washing in 30 ml of water and acidified by dropwise addition of 10% HCl down to pH 7. The final polymer thus obtained is dried at 100° C. under vacuum.

The NMR analysis gives the following results:
$^1$H NMR (500 MHz) $d_6$-DMSO: 7.08-7.09 (d, 2H), 7.17-7.19 (d, 4H), 7.39-7.40 (d, 4H), 7.62-7.64 (m, 6H), 7.80-7.82 (d, 2H), 7.79-7.85 (m, 8H), 8.27-8.28 (s, 2H), 8.65-8.66 (d, 4H),), 8.69-8.70 (d, 2H).

V-4. Manufacture of PEM Membranes

In this test, Polymer 1 membranes are prepared according to the "solvent casting" technique as described below.

The polymer (625 mg), dissolved beforehand in 8 ml of N,N-dimethylacetamide, is filtered through a PTFE (polytetrafluoroethylene) microfilter ("Millipore") having a pore size of approximately 0.45 µm. The polymer solution thus filtered is then run into a mould consisting of two superimposed glass sheets, the upper sheet comprising a recess (dimensions 9 cm×9 cm) with a depth equal to 1 mm; the solution is subsequently heated at 50° C. for 24 h and then at 60° C. for 2 h. The traces of organic solvent are then removed from the membrane thus formed by immersing the latter in a bath of distilled water for approximately 12 h.

After final drying at 60° C. under vacuum for 2 h, a strong and transparent membrane, with a thickness which is equal to approximately 50 µm, is thus obtained, which is ready for characterization.

V-5. Characterization of the PEM Membranes

V-5-A) Proton Conductivity

For the acidification of the membrane (to remind, exchange of the $M^+$ cation by $H^{3o}$), the Polymer 1 is initially immersed in 200 ml of 1.9M $H_2SO_4$ (aq) for 2 h. Use is made of the acid $H_2SO_4$ distilled twice (Sigma Aldrich), in order to avoid traces of metals. Distilled water is subsequently added in several stages (total duration approximately 12 h) in order to reach a pH equal to 7; the membrane is subsequently thus stored in the distilled water overnight (approximately 12 hours).

The proton conductivity of the membrane, expressed in S/cm (Siemens per centimeter) is determined as indicated below.

Membranes in the form of discs with a diameter of 2 cm (thickness 50 µm) are cut out using a hollow punch. The proton conductivity of the membrane is determined by measuring the real part (Ohmic) and the imaginary part (Capacitance) of the complex impedance, within the range of frequencies lying between 100 kHz and 10 Hz (with amplitude of 100 mV AC). The measurements are carried out with an impedance/AC potentiostat (Zahner, Germany). Nyquist graphs are generated by the measurements of a successive stack of one, two, three and up to six membranes (completely humidified) sandwiched between two platinum electrodes having the same circular shape as the membranes.

For each measurement, the value intercepting the real axis of the Nyquist graph is given, that is to say a value of the imaginary component of the impedance at zero. In general, these points are aligned on an affine straight line, the slope of which directly determines the value of the resistance of the membrane. Its ordinate at the origin determines the contact resistance between the membranes and the platinum electrodes. The latter values and the knowledge of the thickness make it possible to calculate in a known way the resistivity of the membrane; the inverse of this value is the conductivity.

Thus tested, the membranes resulting from the Polymer 1 have shown noteworthy proton conductivity values approximately equal to 35 mS/cm at 25° C. (100% humidity), i.e.

approximately 50% of the conductivity value (approximately 70 mS/cm) measured on the commercial membrane ("Nafion® 112"), for its part optimized for a long time, with the same thickness and rigorously tested under the same conditions.

V-5-B) Water Absorption Capacity and Dimensional Stability

Once the membrane has been acidified, it is dried at 100° C. under vacuum for 12 h. Its weight is immediately measured, before it captures atmospheric moisture. The membrane samples are then immersed in distilled water at ambient temperature until saturated (no additional weight gain due to water is observed).

The water absorption capacity, expressed in %, is calculated as the difference between the weight of the wet membrane and the weight of the dry membrane. The dimensional stability, also expressed in %, is the ratio of the main dimension of the dry membrane to the main dimension of the completely humidified membrane.

It is noted that the membranes of the Polymer 1 have a water absorption capacity equal to approximately 20% of their weight, in comparison with a value of approximately 23% for the commercial membrane ("Nafion® 112"). Its dimensional stability is equal to 1%, in comparison with a value of 7% for the control commercial membrane.

In other words, it is found that the membranes resulting from the monomers in accordance with the invention unexpectedly exhibit not only a reduced water absorption capacity but also a noteworthy dimensional stability, so many factors which are determining for the endurance and the chemical stability of the membrane while operating in a PEM fuel cell.

V-5-C) Performance in a PEM Fuel Cell

The performances of the membranes can be tested on a test bed for fuel cells on which the temperature, the pressure, the flow rate and the humidity of the gases can be regulated. The gases used are pure hydrogen and pure oxygen, at a temperature of 65° C.

The fuel cell used in these tests is composed of a single cell comprising the polymer membrane to be tested, positioned between two "GDE" (Gas-Diffusion Electrode) layers, two graphite bipolar plates and two standard electrodes ("ELE 0107" from Johnson Matthey) having a platinum content of approximately 0.4 mg/cm$^2$.

The membrane to be tested is first of all dried between two nonwovens (sterile chamber grade, "Sontara Micropure 100"—supplier DuPont). It is subsequently pressed between two glass plates at 60° C. for 3 h. The MEA assembly is obtained by hot pressing a Pt/C catalysis layer positioned on each side of the membrane (115° C., 125 MPa). At this stage, the MEA assembly can be assembled between two bipolar plates to form a single cell of a fuel cell which is ready to operate when it is fed with hydrogen and oxygen.

For the requirements of the test, the fuel cell is subjected to stationary conditions (0.7 V) or to shutdown and startup or "OCV" (Open Circuit Voltage) situations, in order, in a known way, to subject the membrane to the most aggressive operating conditions (e.g., peroxides, free radicals, and the like) and to deduce therefrom its overall chemical resistance.

FIG. 7 reproduces the "polarization" curve, the voltage of the single cell being recorded as a function of the current density delivered by the fuel cell, on the one hand for the membrane consisting of the Polymer 1 (curve $C_A$) and, on the other hand, for the commercial membrane ("Nafion® 112" polymer, curve $C_B$).

The following comments result from the reading of these two curves:

first of all, at high voltage and zero current (open electrical circuit), it is noted that the polarization voltage is equivalent for the two membranes, which illustrates, to a person skilled in the art, an equivalent permeability to the gases ($O_2$ and $H_2$);

subsequently, slopes of the two curves are observed which are relatively similar in their central linear part (typically between 200 and 800 mA/cm$^2$), the slightly lower slope of the curve $C_A$ being linked to a lower ion conductivity of the membrane, which testifies to a similar electrical performance of the two membranes, without even a particular optimization of the electrodes (anode and cathode) for the specific membrane of the invention.

In conclusion, the monomers of the invention make it possible to manufacture polymers and PEM membranes which, unexpectedly, exhibit a chemical stability and a dimensional stability which are at least equivalent to those of the commercial membranes of the Nafion® type which have, however, been developed for a very long time, as well as an ion conductivity approaching those of these commercial membranes; these polymers additionally exhibit a noteworthy chemical stability and a noteworthy resistance to oxidation.

The invention claimed is:

1. An aromatic perfluoroalkane monomer corresponding to a formula (I):

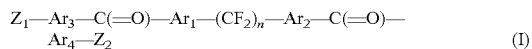

in which:

n is in a range from 1 to 20, $Ar_1$, $Ar_2$, $Ar_3$, $Ar_4$ which are identical or different, represent an unsubstituted phenylene group or a phenylene group substituted with at least one substituent selected from the group consisting of —F, —Cl, —Br, —CN, —CF$_3$, —NO$_2$, —N(CH$_3$)$_2$, —COOH, —COOM, —PO$_3$H, —PO$_3$M, —SO$_3$H, —SO$_3$M, hydroxyl, alkyl, cycloaklyl, perfluoroalkyl, sulphoalkyl, sulphoaryl, aryl, alkylcarbonyl, arylcarbonyl, alkoxyl and aryloxyl, where M is an alkali metal cation, and $Z_1$ and $Z_2$, which are identical or different, represent an electrophilic or nucleophilic polymerizable functional group.

2. The monomer according to claim 1, wherein n is in a range from 2 to 20.

3. The monomer according to claim 1, wherein n is in a range from 2 to 8.

4. The monomer according to claim 1, wherein $Z_1$ and $Z_2$, which are identical or different, are chosen from the group consisting of halogen, hydroxyl, alkoxyl, thiol, carboxyl, carboxylate, amino, sulphonamido, acyl chloride, sulphonyl chloride, sulphonyl fluoride, isocyanate, and combinations thereof.

5. The monomer according to claim 4, wherein the monomer corresponds to a formula (I-2):

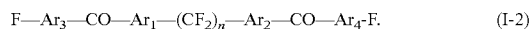

6. The monomer according to claim 4, wherein the monomer corresponds to a formula (I-3):

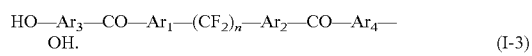

7. The monomer according to claim 1, wherein n is equal to 4.

8. The monomer according to claim 2, wherein n is equal to 4.

9. The monomer according to claim 3, wherein n is equal to 4.

10. The monomer according to claim 4, wherein n is equal to 4.

11. The monomer according to claim 5, wherein n is equal to 4.

12. The monomer according to claim 6, wherein n is equal to 4.

13. The monomer according to claim 1, wherein the monomer is a sulphonic monomer carrying a sulphonic ($-SO_3H$) group or a sulphonate ($-SO_3M$) group, in which M represents an alkali metal cation.

14. The monomer according to claim 13, wherein the sulphonic ($-SO_3H$) group or the sulphonate ($-SO_3M$) group is carried by a phenyl group or a phenylene group, or by a substituent thereof.

\* \* \* \* \*